(12) United States Patent
Ware et al.

(10) Patent No.: US 10,517,527 B2
(45) Date of Patent: Dec. 31, 2019

(54) SLEEP QUALITY SCORING AND IMPROVEMENT

(71) Applicant: BOSE CORPORATION, Framingham, MA (US)

(72) Inventors: Laura Ware, Boston, MA (US); Jonathan Freed, Milton, MA (US); Jack Read, Bolton, MA (US); Debra Reich, Arlington, MA (US); Leela Keshavan, Westborough, MA (US); Brian David Mulcahey, Sudbury, MA (US)

(73) Assignee: BOSE CORPORATION, Framingham, MA (US)

( * ) Notice: Subject to any disclaimer, the term of this patent is extended or adjusted under 35 U.S.C. 154(b) by 28 days.

(21) Appl. No.: 15/267,464

(22) Filed: Sep. 16, 2016

(65) Prior Publication Data
US 2018/0078197 A1    Mar. 22, 2018

(51) Int. Cl.
| | |
|---|---|
| *A61B 5/00* | (2006.01) |
| *A61B 5/0205* | (2006.01) |
| *A61B 7/04* | (2006.01) |
| *A61B 5/024* | (2006.01) |

(Continued)

(52) U.S. Cl.
CPC .......... *A61B 5/4815* (2013.01); *A61B 5/0205* (2013.01); *A61B 5/4809* (2013.01); *A61B 5/4812* (2013.01); *A61B 5/7278* (2013.01); *A61B 7/04* (2013.01); *A61B 5/024* (2013.01); *A61B 5/0816* (2013.01); *A61B 5/1115* (2013.01); *A61B 2560/0252* (2013.01);

(Continued)

(58) Field of Classification Search
CPC ........................... A61B 5/0816; A61B 5/4812
See application file for complete search history.

(56) References Cited

U.S. PATENT DOCUMENTS

| | | | |
|---|---|---|---|
| 4,228,806 A | 10/1980 | Lidow | |
| 5,671,733 A | 9/1997 | Raviv et al. | |
| 5,781,640 A | 7/1998 | Nicolino, Jr. | |

(Continued)

FOREIGN PATENT DOCUMENTS

| | | |
|---|---|---|
| CN | 103519784 B | 11/2015 |
| CN | 105231997 A | 1/2016 |

(Continued)

OTHER PUBLICATIONS

International Search Report and Written Opinion for application No. PCT/US2017/051497 dated Dec. 8, 2017.

(Continued)

*Primary Examiner* — Michael J D Abreu
(74) *Attorney, Agent, or Firm* — Lando & Anastasi, LLP

(57) ABSTRACT

A sleep scoring device is provided for, including a contactless biometric sensor, a processor, memory, and a microphone. The sleep scoring device may detect a user's sleep state by reading signals from the contactless biometric sensor based on at least one of a detected change in heartrate, body movement, or respiration, and log the biometric information. The sleep scoring device may also generate a sleep score for a sleep session based on the latency of the sleep session, the number of detected waking events, the amount of REM sleep, the amount of deep sleep, or the number of times the snooze button was pressed during the sleep session.

22 Claims, 8 Drawing Sheets

(51) Int. Cl.
*A61B 5/08* (2006.01)
*A61B 5/11* (2006.01)

(52) U.S. Cl.
CPC ............... *A61B 2560/0257* (2013.01); *A61B 2560/0475* (2013.01)

(56) References Cited

U.S. PATENT DOCUMENTS

| | | |
|---|---|---|
| 5,928,133 A | 7/1999 | Halyak |
| 6,236,622 B1 | 5/2001 | Blackman |
| 6,662,032 B1 | 12/2003 | Gavish et al. |
| 6,825,769 B2 | 11/2004 | Colmenarez et al. |
| 6,888,779 B2 | 5/2005 | Mollicone et al. |
| 7,248,915 B2 | 7/2007 | Ronnholm |
| 7,637,859 B2 | 12/2009 | Lindback et al. |
| 7,850,619 B2 | 12/2010 | Gavish et al. |
| 8,243,937 B2 | 8/2012 | Nicolino, Jr. et al. |
| 8,280,067 B2 | 10/2012 | Nicolino, Jr. et al. |
| 8,280,068 B2 | 10/2012 | Nicolino, Jr. et al. |
| 8,285,344 B2 | 10/2012 | Kahn et al. |
| 8,379,870 B2 | 2/2013 | Nicolino, Jr. et al. |
| 8,485,982 B2 | 7/2013 | Gavish et al. |
| 8,550,978 B2 | 10/2013 | Ullmann |
| 8,562,526 B2 * | 10/2013 | Heneghan ............ A61B 5/0507 128/920 |
| 8,585,607 B2 | 11/2013 | Klap et al. |
| 8,731,646 B2 | 5/2014 | Halperin et al. |
| 8,855,334 B1 | 10/2014 | Lavine et al. |
| 8,870,764 B2 | 10/2014 | Rubin |
| 8,870,785 B2 | 10/2014 | Muehlsteff et al. |
| 8,964,997 B2 | 2/2015 | Gauger, Jr. |
| 8,992,434 B2 | 3/2015 | Halperin et al. |
| 9,072,437 B2 | 7/2015 | Paalasmaa |
| 9,192,326 B2 | 11/2015 | Kahn et al. |
| 9,192,333 B1 | 11/2015 | Hayes et al. |
| 2002/0080035 A1 | 6/2002 | Youdenko |
| 2002/0186618 A1 | 12/2002 | Kirkpatrick |
| 2003/0095476 A1 | 5/2003 | Mollicone et al. |
| 2003/0142591 A1 | 7/2003 | Baweja et al. |
| 2005/0152223 A1 | 7/2005 | Kawakami |
| 2006/0017558 A1 | 1/2006 | Albert et al. |
| 2006/0102171 A1 | 5/2006 | Gavish |
| 2007/0055115 A1 | 3/2007 | Kwok et al. |
| 2007/0083079 A1 | 4/2007 | Lee et al. |
| 2007/0249952 A1 | 10/2007 | Rubin et al. |
| 2008/0157956 A1 | 7/2008 | Radivojevic et al. |
| 2009/0231964 A1 | 9/2009 | Kraft et al. |
| 2009/0287109 A1 | 11/2009 | Ferren et al. |
| 2009/0292222 A1 | 11/2009 | Ferren et al. |
| 2010/0039399 A1 | 2/2010 | Kim |
| 2010/0087701 A1 | 4/2010 | Berka et al. |
| 2010/0162169 A1 | 6/2010 | Skarp |
| 2010/0226212 A1 | 9/2010 | Gobindram |
| 2010/0281982 A1 | 11/2010 | Liao |
| 2011/0004047 A1 | 1/2011 | Braspenning et al. |
| 2011/0144455 A1 | 6/2011 | Young et al. |
| 2011/0224510 A1 | 9/2011 | Oakhill |
| 2011/0230790 A1 | 9/2011 | Kozlov |
| 2011/0257772 A1 | 10/2011 | Kerber et al. |
| 2011/0264164 A1 * | 10/2011 | Christopherson .... A61B 5/0803 607/42 |
| 2012/0092171 A1 | 4/2012 | Hwang et al. |
| 2012/0327748 A1 | 12/2012 | Lee |
| 2013/0163394 A1 | 6/2013 | Loree, IV |
| 2013/0234823 A1 | 9/2013 | Kahn et al. |
| 2013/0289419 A1 | 10/2013 | Berezhnyy et al. |
| 2013/0289431 A1 | 10/2013 | Gavish et al. |
| 2013/0338446 A1 | 12/2013 | Van Vugt et al. |
| 2014/0088373 A1 | 3/2014 | Phillips et al. |
| 2014/0334645 A1 | 11/2014 | Yun et al. |
| 2014/0371547 A1 | 12/2014 | Gartenberg et al. |
| 2014/0371635 A1 | 12/2014 | Shinar et al. |
| 2015/0141852 A1 | 5/2015 | Dusanter et al. |
| 2015/0164238 A1 * | 6/2015 | Benson ................. G16H 50/30 340/540 |
| 2015/0173671 A1 | 6/2015 | Paalasmaa et al. |
| 2015/0230750 A1 | 8/2015 | McDarby et al. |
| 2015/0258301 A1 | 9/2015 | Trivedi et al. |
| 2015/0263688 A1 | 9/2015 | Nicolino, Jr. et al. |
| 2015/0265212 A1 | 9/2015 | Bruekers et al. |
| 2015/0320354 A1 | 11/2015 | Oakhill |
| 2015/0320588 A1 | 11/2015 | Connor |
| 2015/0367097 A1 | 12/2015 | Gavish |
| 2016/0015315 A1 | 1/2016 | Auphan et al. |
| 2016/0055842 A1 | 2/2016 | DeFranks et al. |
| 2016/0058428 A1 | 3/2016 | Shinar et al. |
| 2016/0151603 A1 | 6/2016 | Shouldice et al. |
| 2016/0217672 A1 | 7/2016 | Yoon et al. |
| 2016/0270718 A1 | 9/2016 | Heneghan et al. |
| 2016/0335886 A1 | 11/2016 | Wei |
| 2017/0039045 A1 | 2/2017 | Abrahami et al. |
| 2017/0087330 A1 | 3/2017 | Kahn et al. |
| 2018/0078197 A1 | 3/2018 | Ware et al. |
| 2018/0078198 A1 | 3/2018 | Reich et al. |
| 2018/0078732 A1 | 3/2018 | Keshavan et al. |
| 2018/0078733 A1 | 3/2018 | Freed et al. |
| 2018/0081527 A1 | 3/2018 | Dolecki et al. |
| 2018/0082550 A1 | 3/2018 | Read et al. |

FOREIGN PATENT DOCUMENTS

| | | |
|---|---|---|
| EP | 2278507 A2 | 1/2011 |
| EP | 2976993 A2 | 1/2016 |
| JP | 2007244597 A | 9/2007 |
| WO | 2005084538 A1 | 9/2005 |
| WO | 2012051630 A2 | 4/2012 |
| WO | 2013093712 A1 | 6/2013 |
| WO | 2013134160 A2 | 9/2013 |
| WO | 2015006364 A2 | 1/2015 |
| WO | 2015008285 A1 | 1/2015 |
| WO | 2015061579 A1 | 4/2015 |
| WO | 2016035073 A1 | 3/2016 |
| WO | 2016122143 A1 | 8/2016 |
| WO | 2016142793 A1 | 9/2016 |

OTHER PUBLICATIONS

International Search Report and Written Opinion for application No. PCT/US2017/051599 dated Jul. 6, 2018.
Android Headlines: "Samsung Galaxy S5—How to Set an Alarm", YouTube, Apr. 28, 2014, pp. 1-3, XP054978390, Retrieved from the Internet: URL:https://www.youtube.com/watch?v=d8MT5Y5US18.

* cited by examiner

SLEEP QUALITY SCORING AND IMPROVEMENT

CROSS-REFERENCE TO RELATED APPLICATIONS

This application relates to U.S. patent application Ser. No. 15/267,552 entitled Intelligent Wake-Up System; U.S. patent application Ser. No. 15/267,567 entitled Sleep Assistance Device; U.S. patent application Ser. No. 15/267,848 entitled Sleep System; U.S. patent application Ser. No. 15/267,858 entitled User Interface for a Sleep System; and to U.S. patent application Ser. No. 15/267,886 entitled Sleep Assessment Using a Home Sleep System; all of which are filed on even date herewith and are incorporated herein by reference.

FIELD

This disclosure relates to systems, methods, and apparatuses for assessing the overall quality of a user's rest in order to provide objective metrics to user to help gauge the quality of their sleep and make recommendations about improving the overall quality of their sleep.

BACKGROUND

Sleeplessness and poor or interrupted sleep may significantly affect a person's health. Poor sleep may be caused by such factors as ambient noise, stress, medical conditions, or discomfort. Thus, there exists a need for a device that can track and assess the overall quality of a user's sleep and make recommendations for improving the quality of their sleep.

SUMMARY

This disclosure relates to systems, methods, and apparatuses for assessing the overall quality of a user's rest in order to provide objective metrics to user to help gauge the quality of their sleep and make recommendations about improving the overall quality of their sleep.

All examples and features mentioned below can be combined in any technically possible way.

In one example, a sleep scoring device is provided for, including a contactless biometric sensor for determining at least one of a heart rate, a respiratory rate, a presence of a user, or movement of a user; a processor; memory; and a microphone. The processor may be configured to, during a sleep session, detect a user's sleep state by reading signals from the contactless biometric sensor based on at least one of a detected change in heartrate, body movement, or respiration, and log information in a sleep record, including biometric information relating to the quality of a user's sleep and environmental factors that may affect the quality of a user's sleep. The sleep scoring device may also generate a sleep score for a sleep session based on consistency of the logged information with corresponding information logged on previous days.

In some examples of the sleep scoring device, the processor is further configured to log one or more sleep start times and one or more sleep stop times within the sleep record. The processor may also be configured to detect the user's presence in a sleep space and to log the time the user entered the sleep space in said sleep record. In other examples, the processor may also be configured to detect sleep stages and to log the start time and stop time of said sleep stages in said sleep record. The sleep stages may include at least one of REM sleep, N-REM sleep, deep sleep, light sleep, stage 1 sleep, stage 2 sleep, stage 3 sleep, or stage 4 sleep. The device may also log environmental factors, including one or more of temperature, noise levels, air pressure, air pollution, or light levels. The processor may also be configured to record detected sounds when sounds are detected at or near the same time as a detected wake-up event of a user.

In other implementations of a sleep scoring device, the processor may be configured to solicit external sleep factors from a user. The processor is may also configured to receive information regarding at least one of said environmental factors from an external database. The external database may be a weather database, a health database, a fitness database, or a calendar database.

In other examples, the processor may be configured to generate a sleep score based on at least one of the detected duration of the sleep or the quality of the sleep. The quality of the sleep can be determined based on one or more of the detected latency of the sleep session, the number of detected waking events during the sleep session, the amount of REM sleep detected during the sleep session, the amount of deep sleep detected during the sleep session, or the number of times the snooze button was pressed during the sleep session. The processor may also be configured to analyze information in the sleep record to identify potential corollaries between instances of sub-optimal sleep and said biometric information, said environmental factors, or said external sleep factors.

A method for monitoring and scoring sleep is also provided-for, including the steps of receiving a plurality of biometric readings of a user from a contactless biometric sensor, recording the plurality of biometric readings within a sleep record, determining the user's sleep state based on the plurality of biometric readings, recording the user's sleep state within the sleep record, receiving a plurality of environmental readings including at least one of a sound level, a light level, an air quality reading, or a temperature, recording the plurality of environmental readings in a sleep record, and determining a sleep score based, at least in part, on the recorded plurality of biometric readings, the recorded sleep state, and the plurality of environmental readings in the sleep record. Some examples of the method also include detecting the user's presence in a sleep space based on the plurality of biometric readings and recording the user's presence in the sleep record. Other examples include detecting sleep stages based on the plurality of biometric readings and recording the sleep stages in the sleep record. Sleep stages may include at least one of REM sleep, N-REM sleep, deep sleep, light sleep, stage 1 sleep, stage 2 sleep, stage 3 sleep, or stage 4 sleep. The environmental readings may include one or more of temperature, noise levels, air pressure, air pollution, or light level readings. External sleep factors may also be received and recorded in the sleep record. Some examples include analyzing information in the sleep record and identifying potential corollaries between instances of sub-optimal sleep and the plurality of environmental readings, the plurality of biometric readings, or the external sleep factors.

A sleep monitoring and scoring system is also provided-for, including a biometric sensor; a microphone; memory; and a processor, coupled to the biometric sensor, the memory, and the microphone. The processor may be configured to detect a user's sleep state by reading signals from the contactless biometric sensor based on at least one of a detected change in heartrate, body movement, or respiration, and wherein said processor is further configured to log information in a sleep record, including biometric information relating to the quality of a user's sleep and environmental factors that may affect the quality of a user's sleep.

BRIEF DESCRIPTION OF THE DRAWINGS

Various aspects of at least one implementation of a sleep quality scoring and improvement system are discussed below with reference to the accompanying figures. The figures are provided for the purposes of illustration and explanation and are not intended as a definition of the limits of the disclosure.

DETAILED DESCRIPTION

It should be understood that the following descriptions are not intended to limit the disclosure to an exemplary implementation. To the contrary, it is intended to cover alternatives, modifications, and equivalents as may be included within the spirit and scope of the described subject matter.

Figure 1A:
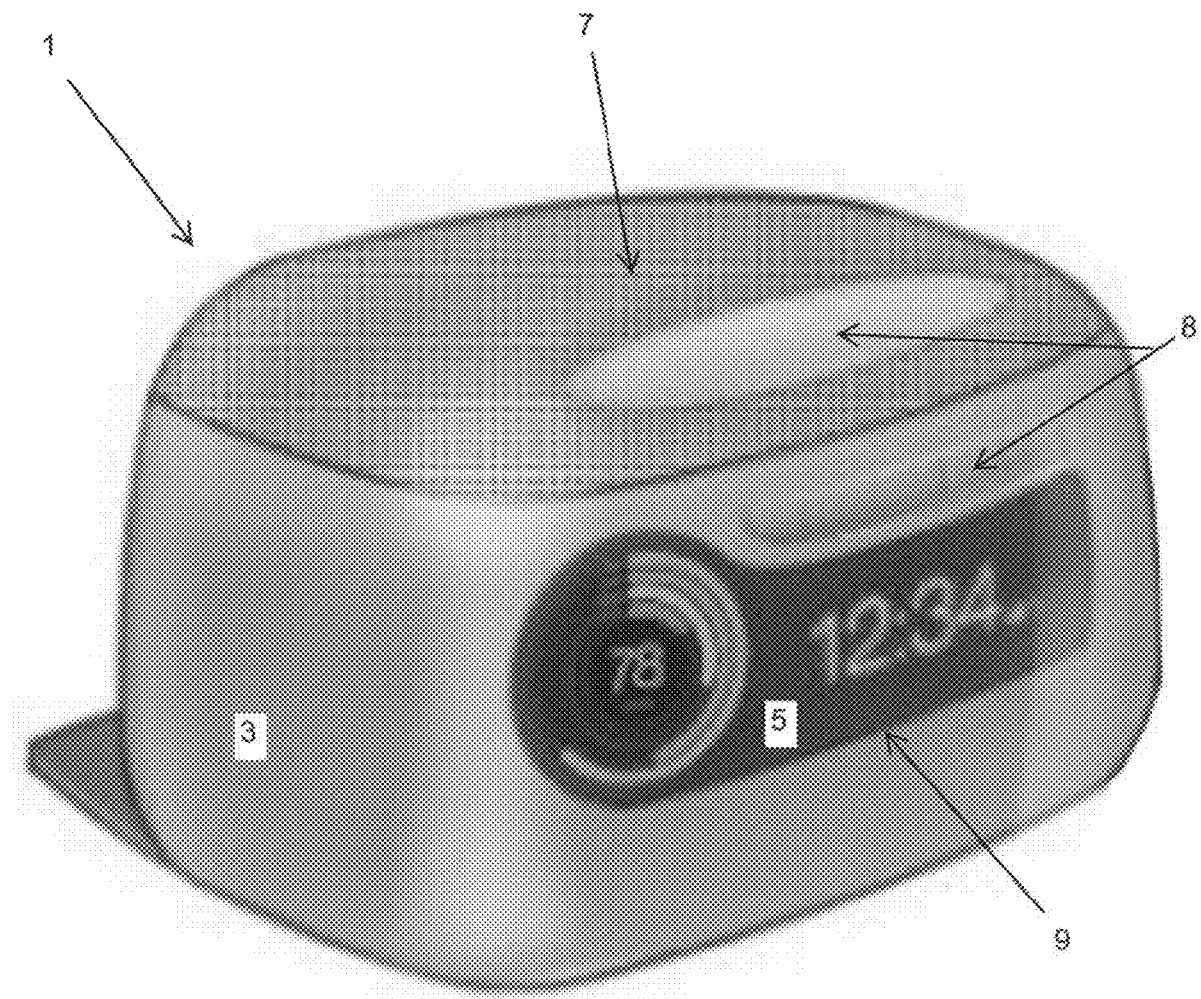
FIG. 1A is a front perspective view of a sleep quality scoring and improvement device with a rectangular housing in one example of the present disclosure.
Figure 1B:
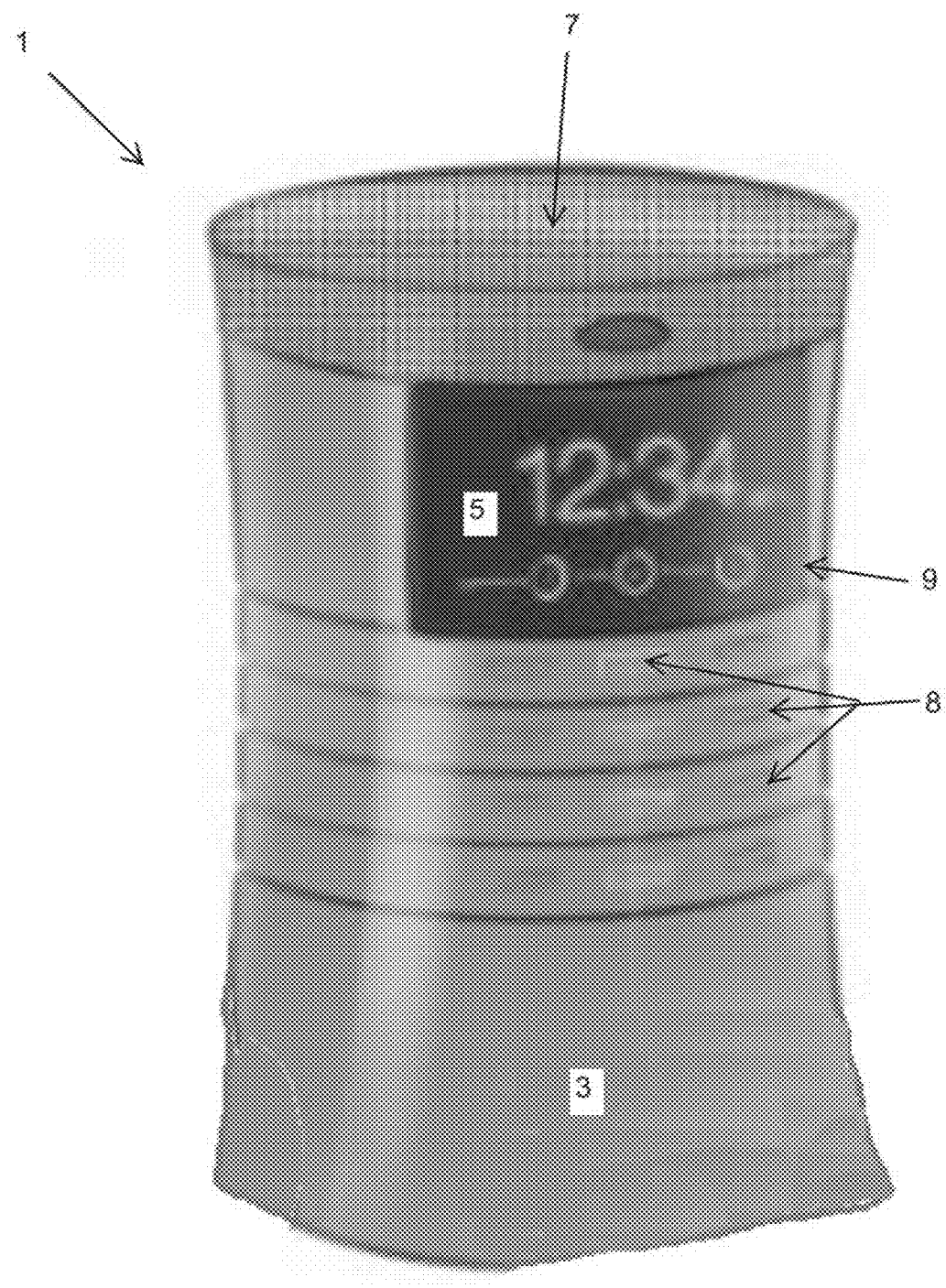
FIG. 1B is a front perspective view of a sleep quality scoring and improvement device with a cylindrical housing in one example of the present disclosure.
Figure 1C:
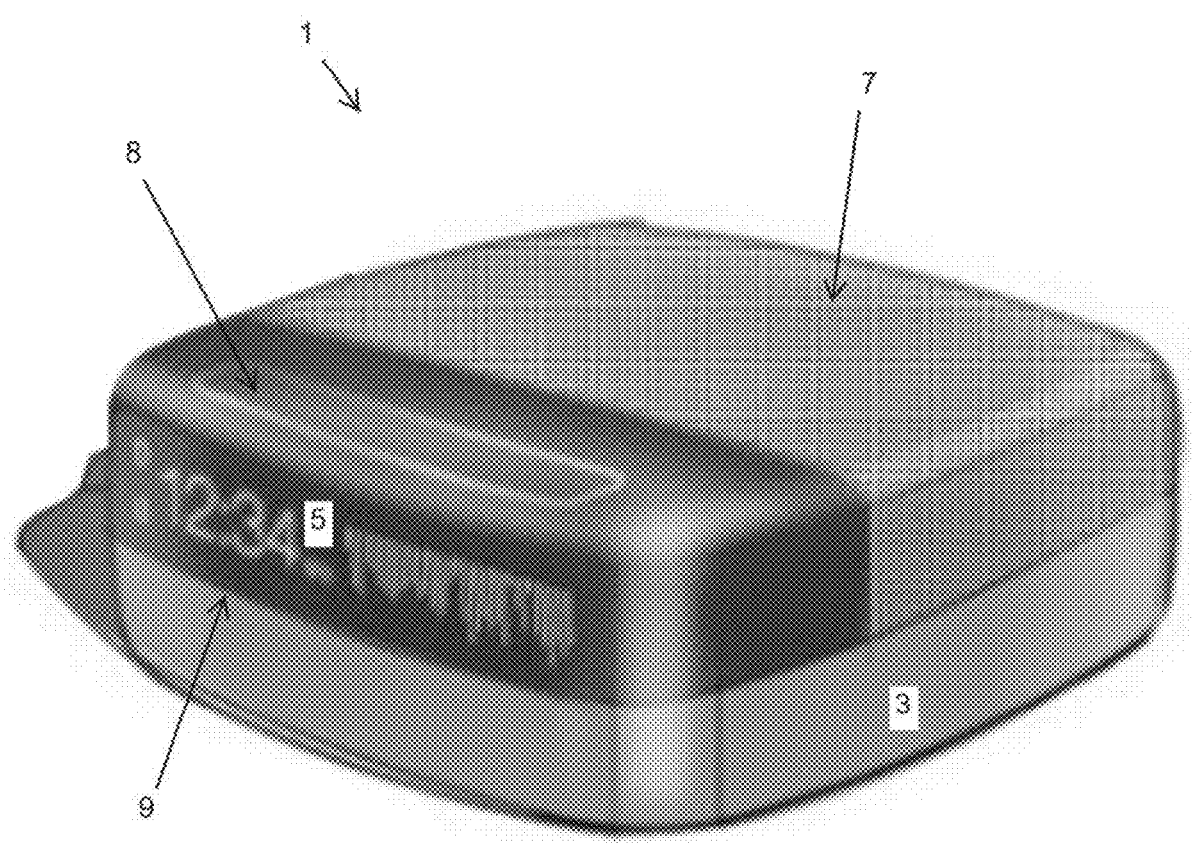
FIG. 1C is a front perspective view of a sleep quality scoring and improvement device with a square housing in one example of the present disclosure.

FIGS. 1A-1C are front perspective views of a sleep scoring device 1 in three examples of the present disclosure. As shown, a sleep scoring device 1 may include a housing 3, a display screen 5, speakers 7, and buttons 8 or a touchscreen 9 for inputting information into the sleep scoring device. A wide variety of forms may be utilized for a sleep scoring device, including a rectangular shape (e.g. FIG. 1A), an elongate cylindrical tower (e.g. FIG. 1B), or a flat square shape (e.g. FIG. 1C). However, as one of ordinary skill in the art will appreciate, any suitable form factor may be utilized that may be suitable for being placed nearby a user while sleeping, such as on a night stand, for example. In such examples, housing 3 may be formed into a suitable shape from any rigid materials, including plastics, metals, wood, or composites.

In some examples, display screen 5 may provide biometric or sleep information gathered by sleep scoring device 1 that may be of interest to a user. Such information may include information regarding the user's biometrics observed during sleep periods, such as information regarding the user's presence, heart rate, heart rate variability, respiratory rate, ambient temperature, movement, snoring, or sleep state over time. This may be direct information or derived information. In some examples, display screen 5 may also include a clock as shown, in FIGS. 1A-1C.

Speakers 7 may comprise any suitable speaker system for generating sounds, as may be familiar to one of ordinary skill in the art. In some examples, speakers 7 may comprise an upwards firing driver along with an acoustic deflector, to provide an omni-directional acoustical experience. Such configurations may be helpful for providing non-directional, room-filling sounds for a soundscape or a white noise while a user is sleeping. Omni-directional sounds systems may be particularly helpful to achieve soothing sounds, a natural wake-up experience, or a consistent listening experience throughout the room. As one of ordinary skill in the art will appreciate, any acceptable sound system for speakers 7 may be employed for producing room-filling sounds, however.

Touchscreen 9 or buttons 8 may comprise any suitable means for delivering inputs to sleep scoring device 1, including a tactile sensor coupled to a surface of housing 3 for detecting the presence of a user's fingers and for detecting pressure, such as when a virtual button on touchscreen 9 is being pressed by a user. Virtual buttons may be displayed on touchpad 9 in a manner familiar to one of ordinary skill in the art in order to allow an operating system to accept input commands from a user. In this manner, sleep scoring device 1 may be configured to accept input commands in a variety of ways and in a variety of contexts, by providing a programmable user interface that may present options and choices to a user via touchpad 9. In other examples, touchscreen 9 may present a permanent display of fixed virtual buttons or include fixed physical buttons 8 for receiving inputs from a user.

In some examples, display screen 5 and a touchscreen 9 may not be necessary or may be reduced in function because a user's smartphone or other external computing device may be used for linking with sleep scoring device 1, displaying information from sleep scoring device 1, accepting inputs, and delivering them to sleep scoring device 1 in order to control its functions. In such a configuration, the display screen 5 and touchscreen 9, if any, may display and control only typical bedside clock-related functions, such as time, alarm, and music selection, or a simplified component of the sleep score, such as just a total score value, may be displayed.

Figure 2:
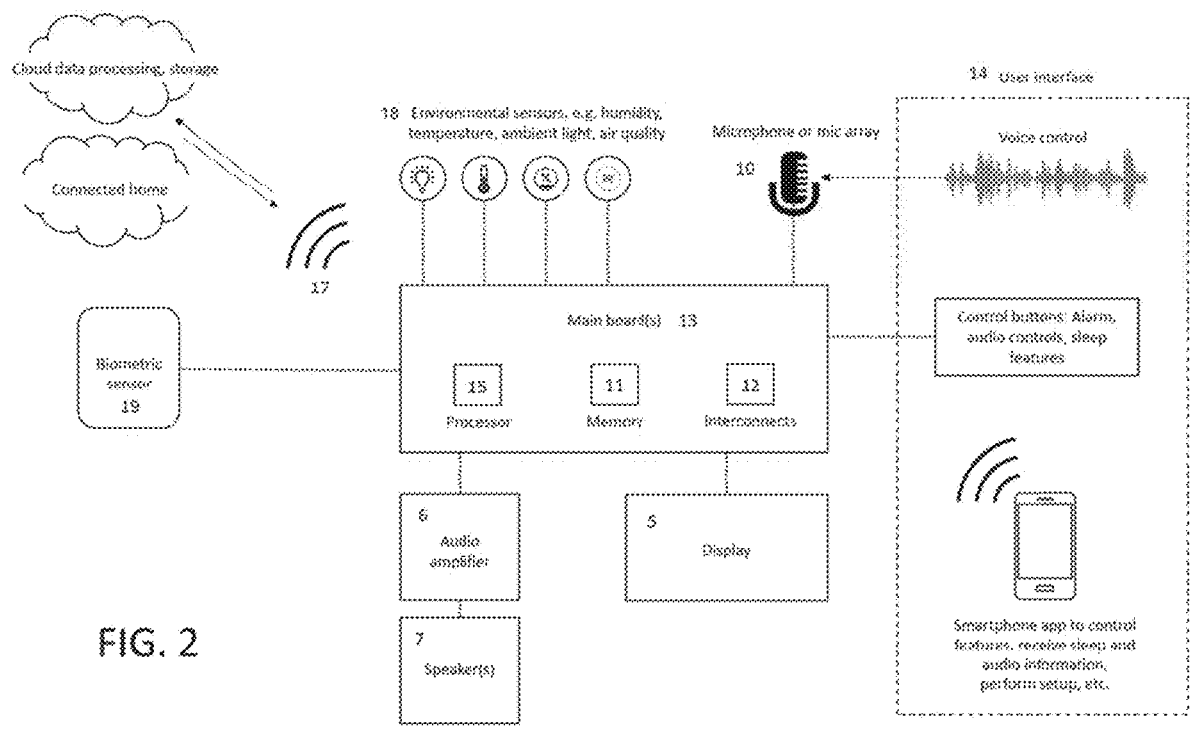
FIG. 2 is a schematic of the components of a sleep quality scoring and improvement device in one example of the present disclosure.

FIG. 2 provides an exemplary schematic of a sleep scoring device, showing its components. As shown, sleep scoring device 1 may include one or more main board(s) 13, including a processor 15, memory 11, and interconnects 12. Main board 13 controls the operation of several other connected components, such as a microphone 10, display screen 5, audio amplifier 6, speakers 7, and buttons 8 or a touchscreen 9 for inputting information into the sleep scoring device. Communications hardware 17 may include any wired or wireless communication means suitable for use with a sleep scoring device, such as WiFi, Bluetooth, USB, micro USB, or any suitable wired or wireless communications technologies known to one of ordinary skill in the art. Main board 13 also receives information from biometric sensor 19 as well as any number of environmental sensors 18, for detecting environmental conditions, such as temperature, humidity, ambient light, and air quality. Main board 13 also receives inputs based on a user's interactions with a user interface 14, which may include voice-activated commands detected by microphone 10; various audio, alarm, and sleep control inputs received from buttons 8 or touchscreen 9; or inputs received from a companion application running on a user's smart phone or other external computing device. The communications hardware 17 may also provide communications with external data sources, such as weather reports, and connected home services providing access to such things as lights, thermostat, locks, and any of the sensors 18.

Microphone 10 may be any suitable microphone for detecting and sampling sounds within a user's bedroom or sleep space, as is known to one of ordinary skill in the art. In some examples, microphone 10 may be an arrayed microphone that is suitable for distinguishing between sounds produced by sleep scoring device 1 and sounds produced externally within the user's bedroom or sleep space. In examples where microphone 10 comprises an arrayed microphone, it may comprise a plurality of omni-directional microphones, directional microphones, or any mixture thereof, distributed about sleep scoring device 1. Microphone 10 may be coupled to processor 15 for simultaneous processing of the signals from each individual microphone in a manner familiar to one of ordinary skill in the art in order to distinguish between sounds produced by sleep scoring device 1 and other sounds within the room and to analyze any external noises for use with sound-masking subroutine 27, as discussed below. Microphone 10 may employ beamforming or other techniques to achieve directionality in a particular direction, for example, towards a sound to be analyzed. Microphone 10 may be employed both for monitoring the user's sleep and for receiving spoken user interface commands.

Biometric sensor 19 remotely detects information about a nearby user, including bed presence, respiration rate, heart rate, or a sleep state among other biometric indicators. In some examples, biometric sensor 19 may be a contactless biometric sensor which may use an RF sensor for directing RF signals towards a user, measuring the strength of the backscattered signal, and analyzing the backscattered signal to determine the state of various vital signs of a user over time. Other contactless biometric techniques may include lasers for measuring minor skin deflections caused by a user's heart rate and blood pressure; or image-based monitoring systems, whereby skin deflections caused by heartbeats and blood pressure may be observed and analyzed over time through a camera. Biometric sensor 19 may be configured to report detected biometric information to processor 15 for storage in memory 11 and to be analyzed for use in the various subroutines described herein.

In other examples, sleep scoring device 1 may also employ a direct biometric sensor as is known to one of ordinary skill in the art. A direct biometric sensor may include probes or contact pads, that may be disposed on or under the user's body or within their mattress or sheets in order to mechanically detect biometric information, such as movement, respiration, heart rate, heart rate variability, blood pressure, and temperature, among others. Such sensors may include accelerometers, other motion sensors, or mechanical sensors such as piezoelectric sensors or other vibration sensors. The biometric information detected by the probes may then be communicated to sleep scoring device 1 using a wired or wireless connection in a manner known to one of ordinary skill in the art. In some examples, a biometric sensor may be placed within earbuds worn by a user. Other implementations may combine both contactless and direct biometric sensors. Mechanical sensors that measure the body through an intervening medium, such as bedding, are included in the category of "contactless" biometric sensors.

Figure 3:
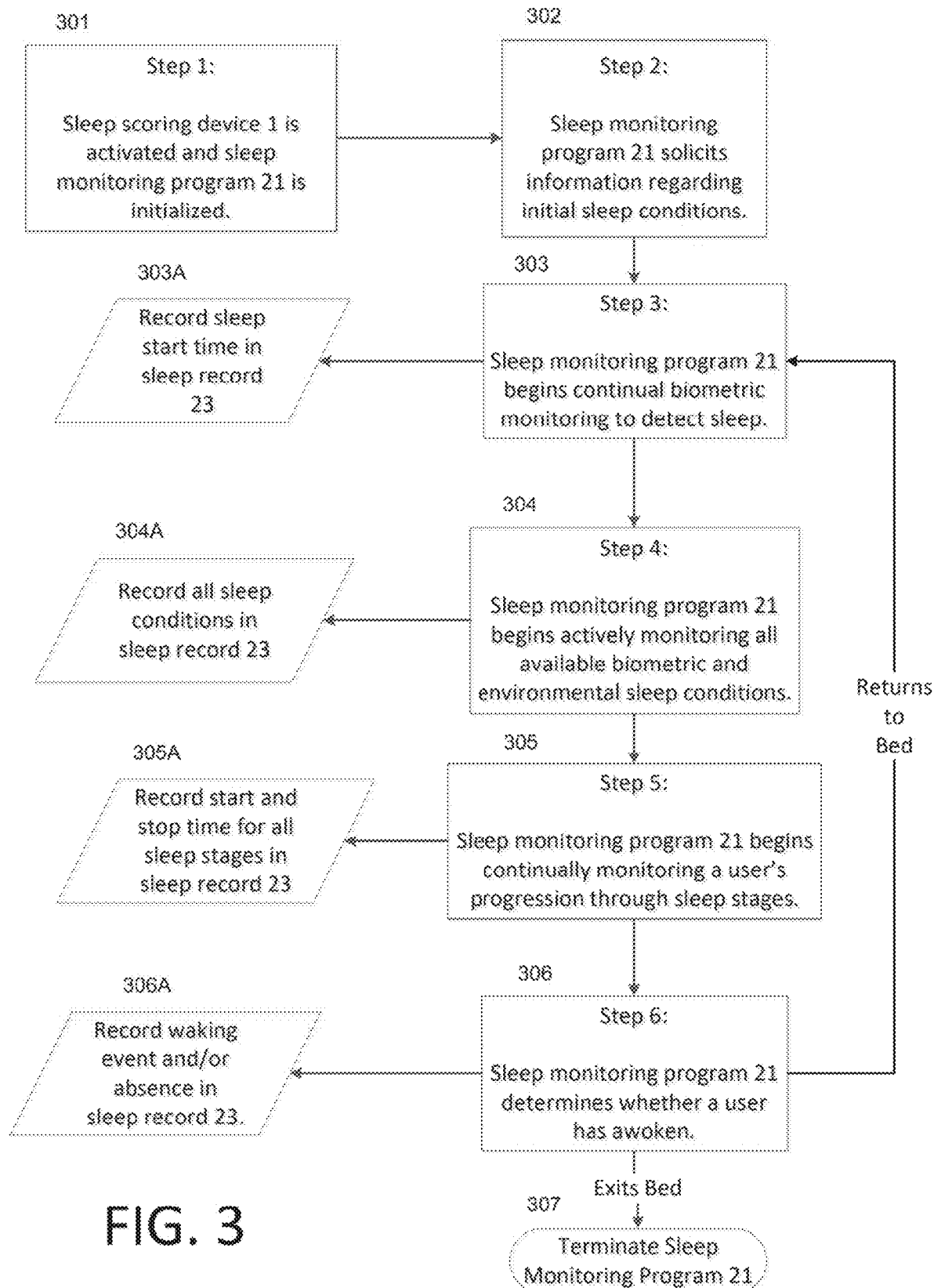
FIG. 3 is a flowchart showing a potential sequence of steps for a sleep quality scoring program in one example of the present disclosure.

Referring now to FIG. 3, in some examples, processor 15 may initiate a sleep monitoring program 21 that includes a series of steps or subroutines to monitor, analyze, and record metrics regarding a user's sleep during sleep sessions. In a first step (box 301 in FIG. 3), sleep scoring device 1 is activated, along with processor 15, which may initialize sleep monitoring program 21. Sleep monitoring program 21 may run on a continuous basis or by default. In some examples, a user may be able to selectively deactivate sleep monitoring program 21 when it is not necessary. In a second step (box 302), processor 15 may determine whether a user is present within their bed or sleep space, which information, along with the relevant time, may be logged in a sleep record 23. Sleep record 23 may be a database for storing and retrieving information relating to a user's sleep throughout a sleep session. Information regarding a user's presence in bed may be useful for providing metrics regarding time spent awake in bed versus time spent sleeping. In other implementations it may be advantageous to periodically monitor only for a user's presence in order to maintain sleep scoring device 1 in a dormant mode in order to expend less power when continual biometric readings are not necessary. Preferably, a user's presence may be detected passively and without the need for a user to manually indicate that they are preparing for sleep (e.g. by pressing a button).

Once a user's presence has been detected, processor 15 may cause user interface screen 5 or an external computing device to solicit user information about their initial sleep conditions in a second step. For example, information regarding the current state of the user or the sleep space may be solicited in a form or via dropdown menus and the like. For example, processor 15 may solicit information regarding what the user ate or drank during the day or before bed, whether the bedroom windows are open, whether a user has showered, whether a user has brushed their teeth, whether the user has recently watched television or read a book, or any other situational information which may be relevant to a user's sleep quality. Any information received by processor 15 through the solicitation process may be logged within sleep record 23. In some instances a user may not wish to fill out a questionnaire regarding their pre-sleep conditions. However, in such instances, processor 15 may employ a user's default settings or simply disregard any omitted initial sleep conditions within sleep record 23 for the current sleep session. Processor 15 may also receive initial sleep conditions either sporadically or consistently without adversely impacting the functionality of the device, but it may be advantageous to input particular information with more diligence during periods when a user is deliberately experimenting with pre-sleep habits, as such information may be useful for providing more effecting sleep coaching, as discussed below. Once baseline information is determined or stable routines are established, it may be preferable to minimize user interaction with the system at the time the user is going to bed. It may also be preferable to minimize interaction when first using the system, so that the user becomes comfortable with the system and develops the habit of allowing it to operate.

In other examples, processor 15 may communicate with external systems, at step 2, in order to retrieve information relevant to a user's day or habits that may be relevant to sleep quality. For example, processor 15 may communicate with exercise tracking applications, such as a database associated with a wearable exercise-tracking device, or other databases for tracking eating habits or other daily activities, such as an online calendar. Home automation systems may also provide information about the state of any windows, the internal temperature, and light levels, to name a few examples. External information may also be gathered and recorded, such as the time of sunset at the user's location and the weather for the day. Any information potentially relevant to sleep quality may be downloaded and stored within sleep record 23 for later analysis.

Once a user's presence has been detected, processor 15 may also begin actively monitoring a user's biometrics on a continual basis in a third step (box 303) in order to determine when a user has fallen asleep. To do so, processor 15 may read signals from biometric sensor 19 to determine whether there has been a measurable change in heart rate, respiration, body movements, or any other biometric indicator of sleep known to one of ordinary skill in the art. Once sleep has been detected, processor 15 may log the time of sleep initiation in sleep record 23 (box 303A).

Once the user has fallen asleep, processor 15 may begin actively monitoring the current sleep conditions throughout the sleep session in a fourth step (box 304). Current sleep conditions may comprise any combination of biometric and environmental variables relevant to sleep which may be measured throughout a sleep session. A user's biometrics may be received from biometric sensor 19 on a continual basis in order to record any relevant variables for tracking the overall quality of a user's sleep over time. For example, variables affecting or indicative of the quality of a user's sleep may include the user's heartrate, respiration rate, any bodily movement, body temperature, blood pressure, or any other biometric information that may be relevant to sleep quality may be monitored by biometric sensor 19 and recorded in sleep record 23 throughout a sleep session (box 304A).

Bedroom environmental variables potentially affecting sleep may also be continually monitored and logged. For example, processor 15 may utilize microphone 10 for monitoring the noise levels or sound attributes within a room or sleep space and may continually log such information in sleep record 23. Microphone 10 may also be utilized by processor 15 to monitor and log any instances of snoring, suspected sleep apnea, sleep talking, or any other events detectable by sound during a sleep session. Instances of such detected noise events may also be detected by processor 15, characterized (in terms of noise level or magnitude), and logged within sleep record 23. Processor 15 may also be configured to record the associated sound(s) for later playback by a user in order to identify any sleep-disruptive sounds and potentially prevent them from reoccurring.

Processor 15 may also receive information from environmental sensors 18, regarding temperature, humidity, ambient light, or other atmospheric conditions within the bedroom. In other examples, environmental sensors 18 may provide information regarding air quality monitors in order to assess the levels of any detectable air pollutants within the sleep space. In other implementations, such information regarding environmental or climate conditions may be gathered through integration with a home-automation system, which may also track and communicate information to processor 15 regarding the temperature readings or thermostat settings within a bedroom or sleep space, along with any other potentially relevant information regarding the home which may impact sleep. Environmental factors may also be gathered from publicly available sources, such as online databases containing local weather, pollution, pollen, seasonal information, or moon phases. Any potentially relevant environmental factors may be received by processor 15 and stored within sleep record 23.

Processor 15 may also accept mechanical indicators of sleep quality. For example, any interactions with the sleep scoring device, itself, may be monitored and logged in sleep record 23, such as instances when a snooze button is depressed or any other settings are adjusted during periods of light sleep or wakefulness. Any interactions with linked, external devices, such as a phone or external computing device, or adjustable aspects of the bed, such as firmness or the temperature of a heating pad, may likewise be monitored by sleep scoring device 1 and any interactions may similarly logged.

While a user is sleeping, processor 15 may also continually receive information regarding a user's progression through various sleep stages in a fifth step (box 305). As one of ordinary skill in the art will appreciate, sleepers typically progress through five stages—stages 1, 2, 3, and 4 (often referred to collectively as non-rapid eye movement or "N-REM" sleep) and rapid eye movement or "REM sleep." Throughout a sleep session, biometric sensor 19 may continually monitor a user's progression through these sleep stages either through direct observation or by determining the likely present sleep stage through observation of other biometric factors, such as heartrate, respiration, and blood pressure. As a user progresses through each sleep cycle, processor 15 may continue to log the present sleep stage over time (box 305A). In other examples, sleep scoring device 1 may not be able to differentiate fully between the above-referenced sleep stages and may instead monitor for and record instances of "light" or "deep" sleep, which may be determined based on analysis of the available biometric indicators in any manner known to one of ordinary skill in the art.

At a sixth step, processor 15 may determine whether a user has awoken, based on the same information used to determine that a user has fallen asleep, such as a measurable change in heart rate, respiration, body movements, or any other biometric indicator of sleep known to one of ordinary skill in the art (box 306). Once a user is detected as having awoken, processor 15 may log the time of waking in sleep record 23 (box 306A) and sleep monitoring program 21 may return to the third step, described above, and begin monitoring whether a user returns to sleep. If processor 15 detects that a user has left the bed or sleep space for more than a brief period of time without returning, the processor may terminate sleep monitoring program 21 and return to an inactive mode whereby biometric sensor 19 only periodically checks to determine whether a user is present.

Figure 4A:
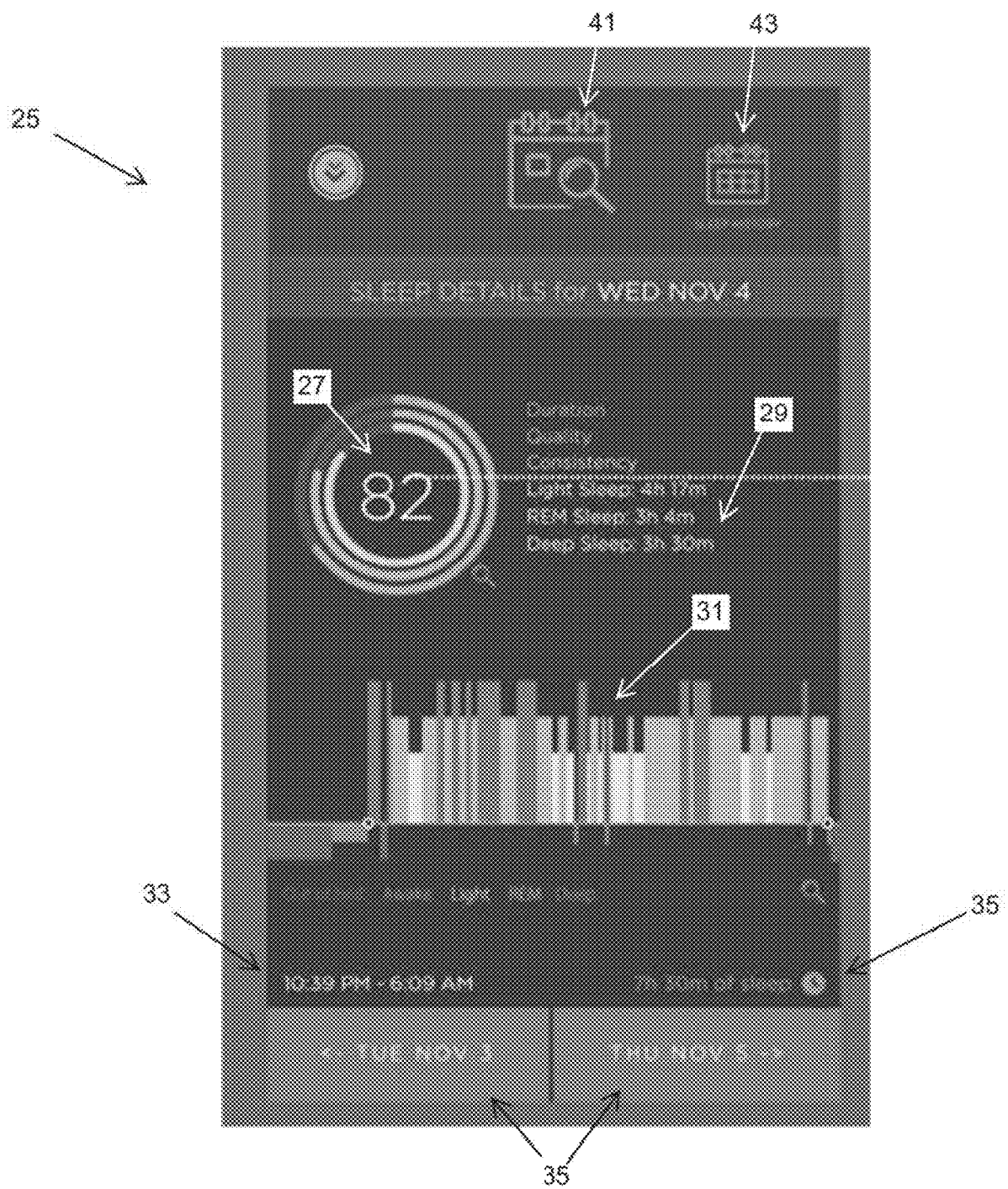
FIG. 4A is a sleep details report in one example of the present disclosure.

Once a sleep session has concluded, processor 15 may generate a sleep details report 25, which may be viewable on user interface screen 5 or an external computing device. FIG. 4A is an example of sleep detail report in one example of the present disclosure. As shown, processor 15 may provide a sleep details report, including a graphical sleep score 27, depicting the overall quality of a user's sleep on that date, as recorded by the system. In some examples graphical sleep score 27 may have color-coded bars representing sleep criteria, such as the duration of the sleep, the quality of the sleep, or the consistency of the sleep, which may all contribute to an overall sleep score. Where available, sleep statistics 29 may also be displayed, such as the amount of light sleep, REM sleep, or deep sleep observed during the prior sleep session. Processor 15 may also include a hypnogram 31 within sleep details report 25, which may provide another graphical depiction of the depth of a user's sleep throughout the night. In some examples hypnogram 31 may be presented by a color-coded time graph representing periods of absence, waking, light sleep, REM sleep, or deep sleep along an x-axis. Different heights along a y-axis may correspond to the relative depth of the sleep during that timeframe. Processor 15 may also include basic information regarding the sleep session within sleep details report 25, such as the sleep timeframe 33 or a sleep duration 35. Where available, buttons 37 may be used to view sleep details reports for other available days recorded within sleep record 23. In other examples, a user may select a date range encompassing a plurality of sleep sessions in order to view relevant sleep statistics within that range, such as the average sleep score, duration, or quality, among others. For example, button 41 may allow users to view sleep details for a single day, whereas button 43 may allow users to see comparative sleep data over multiple days. The data may be available from the sleep system itself, stored in the device implementing the user interface, or retrieved on-demand from a networked resource.

Figure 4B:
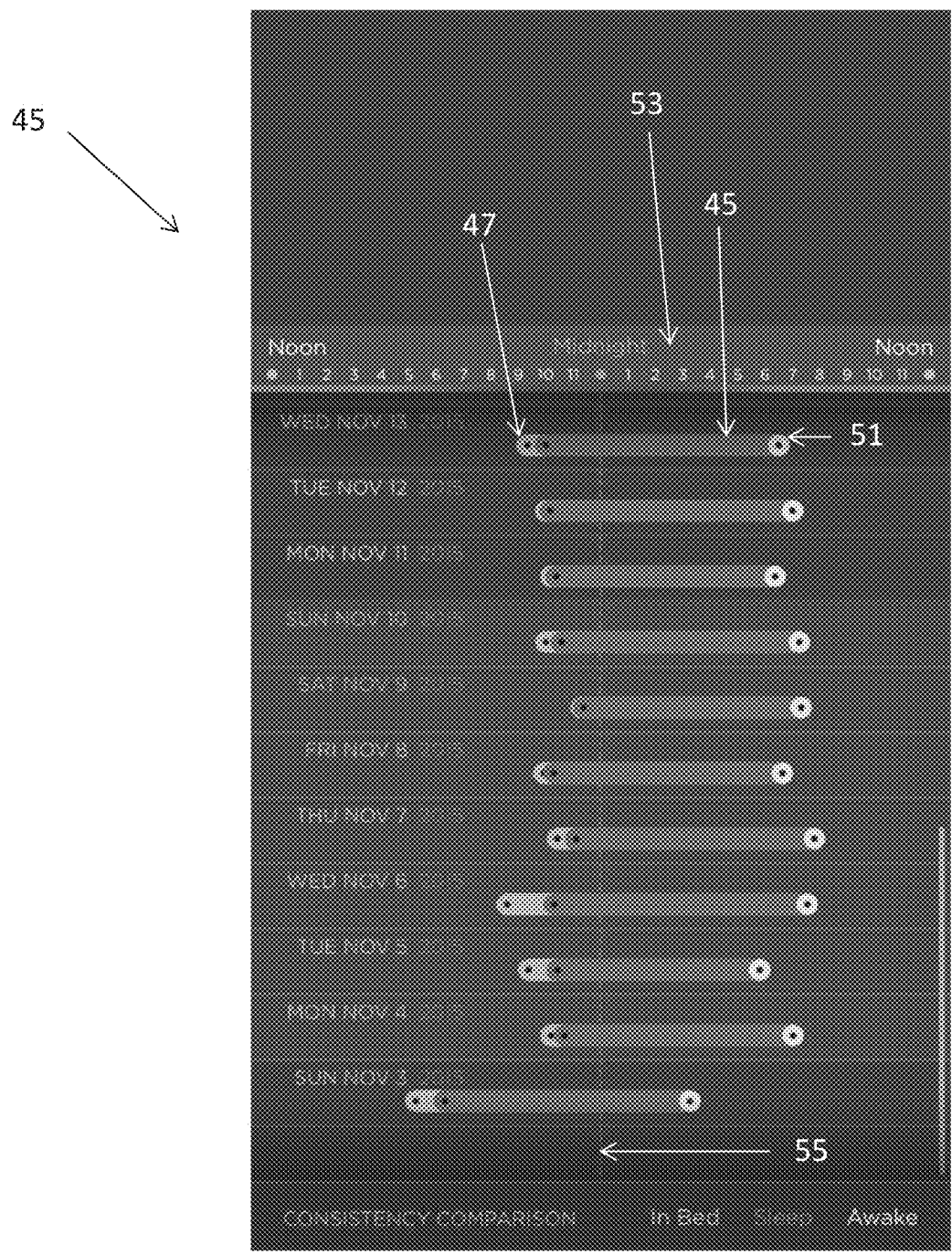
FIG. 4B is a sleep consistency report in one example of the present disclosure.

FIG. 4B shows an example of a sleep consistency report 45 in on example of the present disclosure that may be an example of a report spanning multiple days, which may be accessed by selecting button 43 in FIG. 4A, as previously discussed. In this example, a sleep consistency report 45 provides a graphical representation of a user's observed sleep patterns over multiple days. For example, each sleep session is depicted for multiple days in rows corresponding to separate dates. The sleep sessions are depicted as lines with multiple segments, including an in-bed segment 47 which corresponds to times where the user was detected as being in bed, a sleeping segment 49, which corresponds to times when a user was detected as being asleep, and an waking segment, 51, which corresponds to times when a user was detected as waking from sleep. In some examples, these line segments may be color-coded lines representing the duration of each sleep segment. In this example, the actual colors used and are not shown; color is only used to help visually distinguish the sleep segments, and is redundant with their relative position.

A horizontal time bar 53 may also be included within sleep consistency report 45 to depict the timeframe for any given sleep event or sleep segment within the consistency report. To aid the user in quickly assessing their sleep consistency across multiple days, a vertical time line 55 may also be depicted, which traverses the sleep segments and allows for visual comparison of a user's detected sleep state at the same time on multiple nights. In some implementations, the time line may be fixed at the middle of time bar 53 and the time line 55 may be moved by either dragging the time bar 53 to a desired position or touching a specific hour within the time bar.

Figure 5:
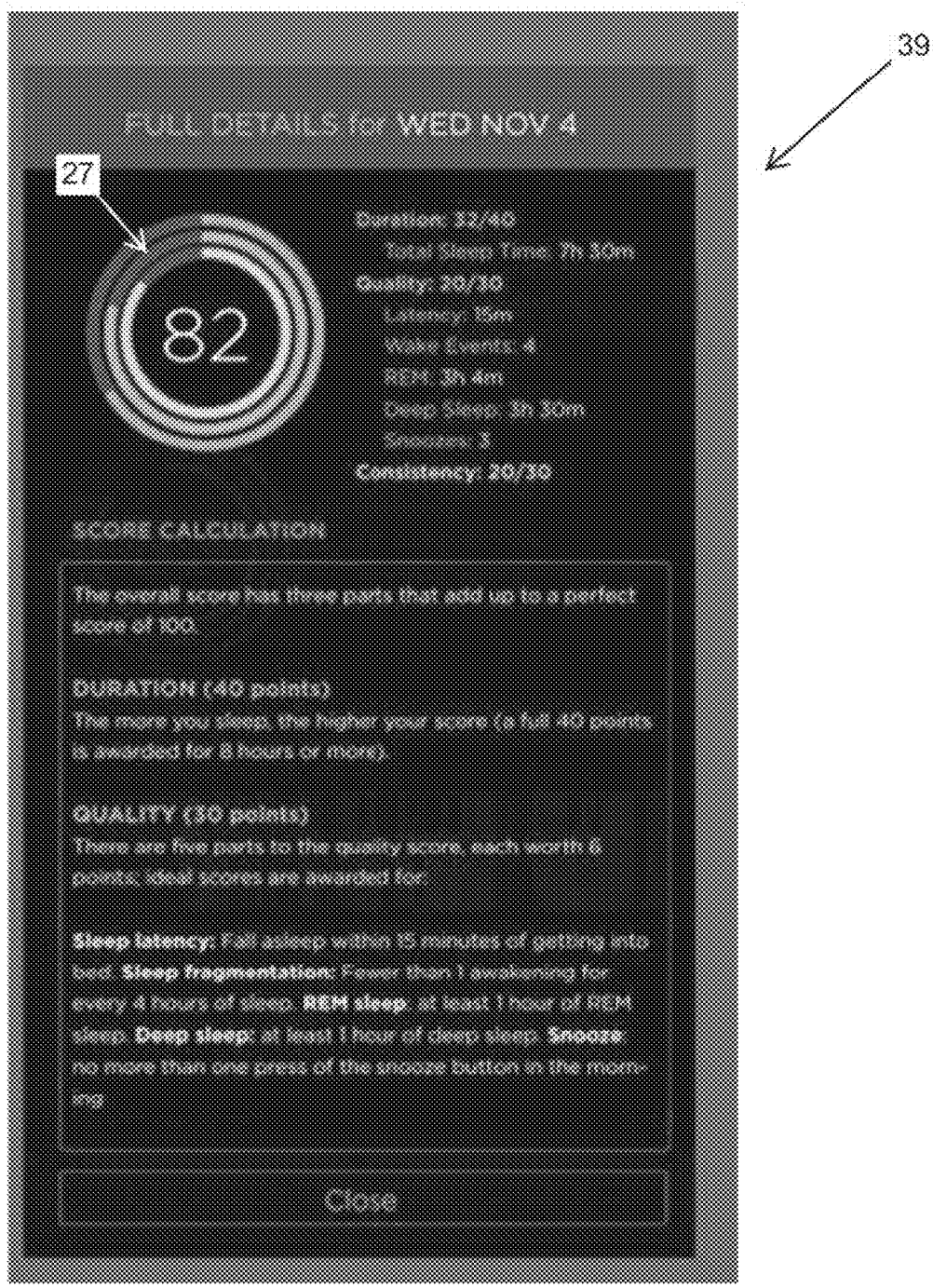
FIG. 5 is a full sleep details report in one example of the present disclosure.

In some examples, processor 15 may also provide a full details report 39, as shown in FIG. 5, which may be accessed by selecting a button or link within sleep details report 25. In some examples, graphical sleep score 27 may serve as a link to a full details report 39. Processor 15 may present a user with further details regarding the data and methodology supporting their sleep score for the selected sleep session in full details report 39. As shown in FIG. 5, a sleep score may be based, in some examples, on three basic sleep criteria, including duration, quality, and consistency. Processor 15 may calculate sleep duration based on the elapsed time of a user's sleep session, with a perfect score reserved for the upper limit of medically recommended amounts of sleep, which may be eight or nine hours or more. Processor 15 determine sleep quality based on several sub-factors, such as latency (e.g. the speed with which a user falls asleep), the number of observed waking events, the amount of observed REM sleep, the amount of observed deep sleep, or any observed mechanical interactions, such as snoozes. These factors may contribute to an overall sleep score using any suitable methodology for scoring and weighting these or any other relevant sleep quality criteria. Finally, processor 15 may calculate sleep consistency based on the overall similarities between sleeping and waking times of a user or any other sleep factors which may be compared night-to-night, based on information stored in sleep record 23. While the present disclosure depicts sleep scoring based on the criteria of duration, quality, and consistency, any combinations of sleep criteria known to one of ordinary skill in the art may be evaluated to determine an overall sleep score.

Any available information may also be viewed, reported, access, compared, or exported from sleep record 23 in any suitable manner known to one of ordinary skill in the art. For example, processor 15 may generate additional reports from sleep record 23 on a daily, weekly, monthly, or yearly basis and may provide a graphical depiction of a user's sleep score alongside any other tracked information stored in sleep record 23, such as recorded sound levels, average caffeine consumption, daily exercise or calorie intake. Such graphical representations of a user's sleep score alongside information relating to a user's environmental factors or habits may allow a user to identify factors that may be adversely affecting sleep. These reports may be selectively generated for a user or may be periodically communicated to a user via user interface 5, email, or via a companion application on an external computing device.

In some examples of this disclosure, processor 15 may also execute a "sleep coaching" engine 41. Through sleep coaching engine 41, processor 15 may periodically analyze the user's sleep history (including biometric, environmental, and user-input variables) in order to identify potential correlations between such variables and instances of diminished or sub-optimal sleep scoring. Processor 15 may also compare observations against publicly available databases of known conditions that may influence sleep in order to identify potential sleep conditions or known solutions to sleep problems. After periodically analyzing the user's sleep data, processor 15 may communicate its findings or suggestions for changes a user can make to improve their sleep, for example through adjusting settings of sleep scoring device 1, itself, adjusting other aspects of the environment, such as thermostat settings, or by recommending that the user alter behaviors that may be adversely affecting sleep. In other instances of the sleep coaching engine 41, processor 15 may proactively assess sleep conditions at the beginning of a sleep session or using publicly available information about upcoming environmental factors to make emergency recommendations when a user is preparing to sleep. For example, if a user or a home automation system indicates that a window is open and other information indicates that rain or a high pollen count is predicted during the upcoming sleep session, processor 15 may send an emergency warning to a user to shut their window. Of course, such periodic interactions may be limited or deactivated by a user according to their preferences.

One of skill in the art will appreciate that the systems, methods and apparatuses outlined above may include various hardware and operating software, familiar to those of skill in the art, for running software programs as well as communicating with and operating any devices, including, for example, a biometric sensor, environmental sensors, a user interface, a computer network, a sound system, and any other internal or external devices. Such computerized systems may also include memory and storage media, and other internal and external components which may be used for carrying out the operations of this disclosure. Moreover, such computer systems may include one or more processors for processing and controlling the operation of the computer system, thus, embodying the processes of this disclosure. To that end, the processor, associated hardware and communications systems may carry out the various examples presented herein.

While the disclosed subject matter is described herein in terms of certain exemplary implementations, those skilled in the art will recognize that various modifications and improvements can be made to the disclosed subject matter without departing from the scope thereof. As such, the particular features claimed below and disclosed above can be combined with each other in other manners within the scope of the disclosed subject matter such that the disclosed subject matter should be recognized as also specifically directed to other implementations having any other possible permutations and combinations. It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed:

1. A sleep scoring device comprising:
   a contactless biometric sensor for determining at least one of a heart rate, a respiratory rate, a presence of a user, or movement of the user;
   a processor;
   memory; and
   a microphone;
   wherein said processor is configured to, during a sleep session, detect the user's sleep state by reading signals from said contactless biometric sensor based on at least one of a detected change in heartrate, body movement, or respiration, log information in a sleep record, including biometric information relating to the quality of the user's sleep and environmental factors that may affect the quality of the user's sleep,
   generate and display a numerical sleep score for said sleep session based on consistency of the logged information with corresponding information logged on previous days, and
   generate a sleep consistency report based on the sleep record, the sleep consistency report illustrating comparative sleep data of the user over multiple days as graphical representations of sleep patterns of the user, each graphical representation being representative of sleep patterns of the user in a single sleep session.

2. The sleep scoring device of claim 1, wherein said processor is further configured to detect sleep stages and to log a start time and a stop time of said sleep stages in said sleep record.

3. The sleep scoring device of claim 2, wherein said sleep stages comprise at least one of REM sleep, N-REM sleep, deep sleep, light sleep, stage 1 sleep, stage 2 sleep, stage 3 sleep, or stage 4 sleep.

4. The sleep scoring device of claim 3, wherein said environmental factors comprise one or more of temperature, noise levels, air pressure, air pollution, or light levels.

5. The sleep scoring device of claim 4, wherein said processor is further configured to record detected sounds when sounds are detected at or near a same time as a detected wake-up event of the user.

6. The sleep scoring device of claim 1, wherein said processor is further configured to log one or more sleep start times and one or more sleep stop times.

7. The sleep scoring device of claim 6, wherein said processor is further configured to detect the user's presence in a sleep space and to log a time the user entered the sleep space in said sleep record.

8. The sleep scoring device of claim 1, wherein said processor is further configured to receive information regarding at least one of said environmental factors from an external database.

9. The sleep scoring device of claim 8, wherein said external database comprises a weather database, a health database, a fitness database, or a calendar database.

10. The sleep scoring device of claim 1, wherein said processor is further configured to generate the sleep score based on at least one of a detected duration of the sleep or the quality of the sleep.

11. The sleep scoring device of claim 10, wherein the quality of the sleep is determined based on one or more of a detected latency of the sleep session, a number of detected waking events during the sleep session, an amount of REM sleep detected during the sleep session, an amount of deep sleep detected during the sleep session, or a number of times a snooze button was pressed during the sleep session.

12. The sleep scoring device of claim 1, wherein said processor is further configured to solicit external sleep factors from the user.

13. The sleep scoring device of claim 1, wherein said processor is further configured to analyze information in said sleep record and to identify potential corollaries between instances of sub-optimal sleep and said biometric information, said environmental factors, or external sleep factors.

14. The sleep scoring device of claim 1, wherein said processor is further configured to generate the sleep score based on at least on a number of times a snooze button was pressed during the sleep session.

15. A method for monitoring and scoring sleep comprising:
    receiving a plurality of biometric readings of a user from a contactless biometric sensor;
    recording said plurality of biometric readings within a sleep record;
    determining said user's sleep state based on said plurality of biometric readings;
    logging said user's sleep state within said sleep record;
    determining and displaying a numerical sleep score based, at least in part, on consistency of the logged information with corresponding information logged on previous days; and
    generating a sleep consistency report based on the sleep record, the sleep consistency report illustrating comparative sleep data of the user over multiple days, the sleep consistency report including graphical representations of sleep patterns of the user for multiple respective days, each graphical representation being representative of sleep patterns of the user in a single sleep session.

16. The method for monitoring and scoring sleep of claim 15, further comprising detecting said user's presence in a sleep space based on said plurality of biometric readings and recording the user's presence in said sleep record.

17. The method for monitoring and scoring sleep of claim 16, further comprising detecting sleep stages based on said plurality of biometric readings and recording said sleep stages in said sleep record.

18. The method for monitoring and scoring sleep of claim 17, wherein said sleep stages comprise at least one of REM sleep, N-REM sleep, deep sleep, light sleep, stage 1 sleep, stage 2 sleep, stage 3 sleep, or stage 4 sleep.

19. The method for monitoring and scoring sleep of claim 15, further comprising:
   receiving a plurality of environmental readings including at least one of a sound level, a light level, an air quality reading, or a temperature; and
   recording said plurality of environmental readings in the sleep record.

20. The method for monitoring and scoring sleep of claim 19, further comprising receiving external sleep factors and recording them in said sleep record.

21. The method for monitoring and scoring sleep of claim 20, further comprising analyzing information in said sleep record and identifying potential corollaries between instances of sub-optimal sleep and said plurality of environmental readings, said plurality of biometric readings, or said external sleep factors.

22. A sleep monitoring and scoring system comprising:
   a biometric sensor;
   a microphone;
   memory; and
   a processor, coupled to the biometric sensor, the memory, and the microphone, the processor being configured to detect a user's sleep state during a sleep session by reading signals from said contactless biometric sensor based on at least one of a detected change in heartrate, body movement, or respiration, and wherein said processor is further configured to log information in a sleep record, including biometric information relating to the quality of a user's sleep and environmental factors that may affect the quality of a user's sleep, to generate and display a numerical sleep score for said sleep session based on consistency of the logged information with corresponding information logged on previous days, and to generate a sleep consistency report based on the sleep record, the sleep consistency report illustrating comparative sleep data of the user over multiple days, the sleep consistency report including graphical representations of sleep patterns of the user for multiple respective days, each graphical representation being representative of sleep patterns of the user in a single sleep session.

* * * * *